United States Patent [19]
Hessel et al.

[11] Patent Number: 5,797,922
[45] Date of Patent: Aug. 25, 1998

[54] UMBILICAL CORD CLAMPING DEVICE

[75] Inventors: Stephen R. Hessel, Fountain Valley; Michael Katz, Port Richmond, both of Calif.

[73] Assignee: Balagan Medical Inc., Huntington Beach, Calif.

[21] Appl. No.: 821,111

[22] Filed: Mar. 20, 1997

Related U.S. Application Data

[63] Continuation of Ser. No. 597,607, Feb. 6, 1996, abandoned.
[51] Int. Cl.[6] .................................................. A61B 17/00
[52] U.S. Cl. .................................... 606/120; 606/142
[58] Field of Search .............................. 606/119, 120, 606/142, 157, 174, 205–211

[56] References Cited

U.S. PATENT DOCUMENTS

| | | | |
|---|---|---|---|
| 352,245 | 11/1886 | Hullhorst | 606/142 |
| 2,524,337 | 10/1950 | Whittaker | 606/120 |
| 4,428,374 | 1/1984 | Auburn | 606/120 |
| 4,781,188 | 11/1988 | Collins | 606/120 |
| 5,178,624 | 1/1993 | Kyun | 606/120 |

*Primary Examiner*—William Lewis
*Attorney, Agent, or Firm*—Knobbe, Martens, Olson & Bear, LLP

[57] ABSTRACT

A clamping device for securing a pair of clamps to the umbilical cord of a newly born infant includes pressure plates to remove blood from the section of the cord between the clamps. Thus, there is a greatly reduced risk of infection from blood squirting out upon the cutting of the cord during delivery of the infant.

28 Claims, 7 Drawing Sheets

UMBILICAL CORD CLAMPING DEVICE

This application is a continuation of U.S. patent application Ser. No. 08/597,607, filed Feb. 6, 1996 now abandoned.

BACKGROUND OF THE INVENTION

1. Field of the Invention

The present invention relates generally to the field of obstetrical instruments, and, in particular, to an umbilical cord clamping device.

2. Description of the Related Art

The delivery of a newborn infant, either vaginally or through cesarean section, always entails the cutting of the umbilical cord which was the lifeline connecting the child to its mother. The cord is normally clamped twice, first close to the abdomen of the infant and secondly about an inch closer to the placenta which is usually still within the mother's uterus. The cord is then cut between the two clamps. The clamp closer to the infant is usually formed of lightweight plastic and is small so that its size and weight on the infant neither interferes with the cord stump healing nor causes an umbilical hernia. A reusable clamp is typically used on the placental cord end in order to prevent its hemorrhaging during the delivery of the placenta and other surgical procedures on the mother.

The umbilical cord is a somewhat tough, gelatinous, fibrous tissue member having two arteries and a vein, and the cord is usually covered with at least amniotic fluid and blood upon delivery. The diameter of the cord varies from about one-quarter to one inch, with greater force required to secure the clamps onto the thicker cords. Attachment of the clamps to the cord is therefore made complicated by the slippery nature of the cord as well as the variability in the cord size. Additional difficulty arises when delivery is performed by a lone person who must use one hand to hold the infant and the other to attach the clamps.

Present cord clamp applying devices may provide simultaneous clamping and cutting of the umbilical cord. One, or often two, clamps are secured within the device using an external spring or a specialized configuration of the device corresponding to specially designed clamps. The clamping and cutting devices typically use disposable clamps. Both the devices and clamps are usually of complex design and are correspondingly more expensive. Reusable devices require additional handling and sterilization which contribute to possible misalignment and damage to the devices.

These combination clamping and cutting devices require accurate placement of the clamps at a first attempt, since the cut is made as the clamps are attached to the cord. Many doctors prefer to see the clamped area to be cut before actually cutting the cord. If the clamp is placed too closely to the infant's abdomen, abdominal tissue may be crushed by the clamp or there may be insufficient room to allow for the shrinking of the infant cord end toward the abdomen.

Further, if only a single clamp is applied by the device, it is supposed to be on the infant cord end so that the placental cord end may be exposed for purposes of obtaining blood samples or the like. If the clamp is accidentally put on the placental cord end, there is a danger of infection, delayed healing or other problems caused by the exposed cord of the newborn. Whether one or two clamps are attached, and whether cutting is performed simultaneously or not, the clamps must be securely closed on the cord so that they do not slip off or pop open before a time designated by the doctor. The clamps are generally removed from the device, after attachment to the cord, without a subsequent action by the user.

Another consideration in the clamping and cutting of the umbilical cord is the probability of exposure to blood and therefore bloodborne diseases. Doctors and nurses wear protective clothing, including gloves and masks, and sometimes goggles, to prevent possible infection from uterine blood and other fluids from the mother, as well as blood squirting from the cut umbilical cord. Although HIV-II, commonly known as AIDS, is widely feared, hepatitis is more likely to be spread through contact with the blood. Other persons in the vicinity of the delivery without proper protection, such as the infant's father, are at even greater risk of contact with the blood.

One method of removing the blood in the cord is by "milking" the area to be cut. However, milking is not always effective, since there is blood flow from the infant and post partum contractions of the placenta which serve to continually replenish the volume of blood in the cord. Also, this procedure requires two hands to be effective and takes some time. In an emergency, the doctor will not hesitate to bypass this procedure and quickly cut the cord to attend to the infant or mother while accepting the potential risk arising from blood squirting when the umbilical cord is cut.

SUMMARY OF THE INVENTION

An umbilical cord clamping device of the present invention comprises a pliers-like unit for attaching a pair of resilient clamps prior to severance of the cord and has a handle assembly having a pair of handle portions and a clamp holder assembly having holding members. The handle portions are substantially identical and are attached to pivot at a point intermediate a proximal end of the handle portions which are grasped by a user and a distal end of the handle portions to which are attached the holding members. Each member has a pair of receptacles for receiving one arm of each clamp and a pressure plate positioned between each pair of receptacles for removal of blood from between the clamps on the umbilical cord.

The receptacles of the holding members hold each clamp's arms in a position compressed from the original arm positions at manufacture. Thus, the clamps are retained in the holding members without a latch or external constraining mechanism. The clamps are spaced apart to provide clamping of the separated infant and placental (maternal) cord ends, and the pressure plates on the opposing members effectively remove blood from therebetween so that the severance of the cord involves the release of a minimal amount of blood.

A preferred embodiment of the present invention comprises holders separately formed from the handle portions. Alternatively, the holders and handle portions may be integrally formed so that the device comprises two one-piece sections which are pivotably attached and receive the clamps. Preferably, the holders and handle portions are formed from molded plastic or other resilient material. The preferred embodiment further includes pressure plates which are exterior to the clamps held in the members, so that the plates make first contact with the cord for squeezing the blood outwardly from between the clamps.

It is most preferable to have guides for positioning the cord between the holders during the closure of the clamps. In addition, it is preferred that the plates are initially cantilevered within the holders, and the free ends constrained within the holders during closure to form simply supported beam-like members which deflect against the cord.

An important feature of the present invention is the compression by the plates of the cord in order to minimize the amount of blood in the cord between the clamps. That is, the pressure plates squeeze the blood away from between the clamps. This substantially eliminates the blood which issues from the cord when it is severed during delivery of the infant. This feature is especially appreciated by personnel in the vicinity of the delivery who would otherwise be splattered by potentially infectious bodily fluid.

Another important feature of the present invention is the retention of the resilient clamps within the holder assembly by compression of the clamp arms from their original, substantially orthogonal relative positions. The holding members of the device are preferably limited to opening approximately 50 degrees to receive the umbilical cord, and thus compress and contain the clamp arms. After the clamps are closed upon the cord and locked into place, the user easily rotates the handles of the device and removes the holders from around the clamps. Clamps manufactured by Hollister Inc. in Chicago, Ill., for example, are advantageously used with the present invention and are commonly available.

Yet another important feature of the present invention is a closure indicator for easy verification by the user, by feel, sight and sound, that the clamps have been sufficiently closed on the cord. As the clamps make the final locking connection onto the cord, a snapping sound of the indicator on the device is accompanied by a slightly increased resistance by the device which is felt by the user. The user may also view the indicator to verify that it is somewhat distended, indicating completion of the clamp closure.

Further advantages and applications will become apparent to those skilled in the art from the following detailed description and the drawings referenced herein.

DETAILED DESCRIPTION OF THE PREFERRED EMBODIMENT

The hospital environment where a newborn child is delivered may be relaxed and almost casual for a routine delivery, or the atmosphere may be charged with the commotion and uncertainty of an emergency situation. In either situation, and most particularly in the latter, medical personnel prefer to deal with familiar equipment and dependable medical instruments. An umbilical cord clamping device 20 constructed in accordance with the present invention, shown in use in FIG. 1, resembles other obstetrical tools with its pliers-like design. The device 20 provides easy, single-handed operation with features described herein that afford reliable, secure clamping of an umbilical cord 10. The device 20 further provides for a minimal amount of blood released upon a later cord cutting by either a doctor or nurse or the proud father. Thus, exposure to possible infection from bloodborne disease is minimized.

Umbilical Cord Clamping Device

Figure 1:
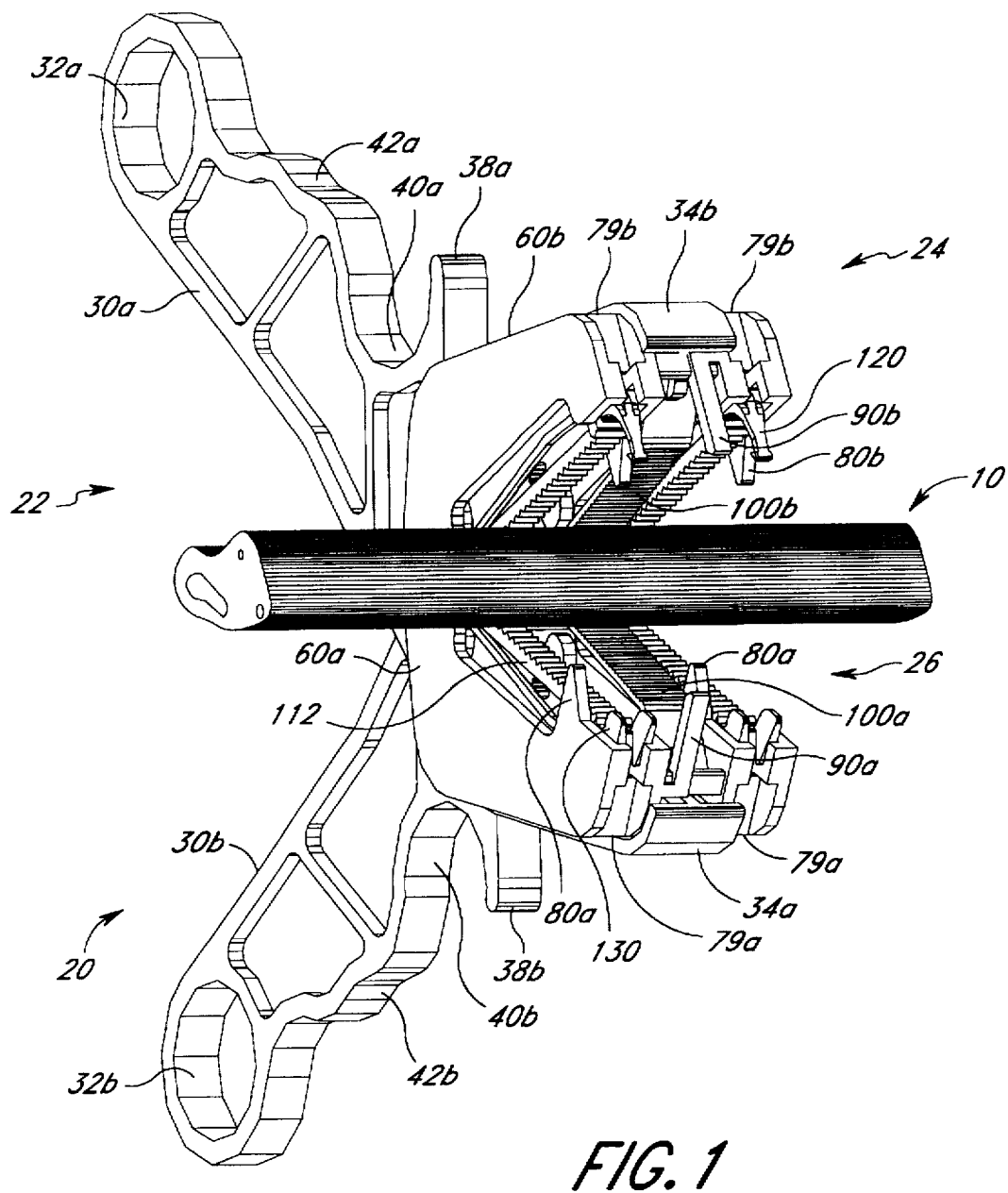
FIG. 1 is a perspective view of an umbilical cord clamping device of the present invention prior to closure about the cord.

The perspective view of FIG. 1 shows the umbilical cord 10 just prior to its being clamped in a mouth formed at a distal end of a handle assembly 22 by a clamp holder assembly 24. A user's hand (not shown) grasps a proximal end of the handle assembly 22 and easily closes the mouth. Pressure plates 100 on the holder assembly 24 compress the cord 10 to remove blood from between a pair of clamps 26 which are secured onto the cord 10. Indicators 90 provide assurance to the user that the clamps 26 are adequately closed. Preferably, the assemblies 22, 24, as well as the clamps 26, are formed of molded plastic or other resilient material. The clamps 26 are fastened on the cord 10 so that after the cord 10 is severed, between the pair of clamps 26, blood from the infant and/or the placenta is prevented from issuing out of the cord ends.

Handle Assembly

Figure 2:
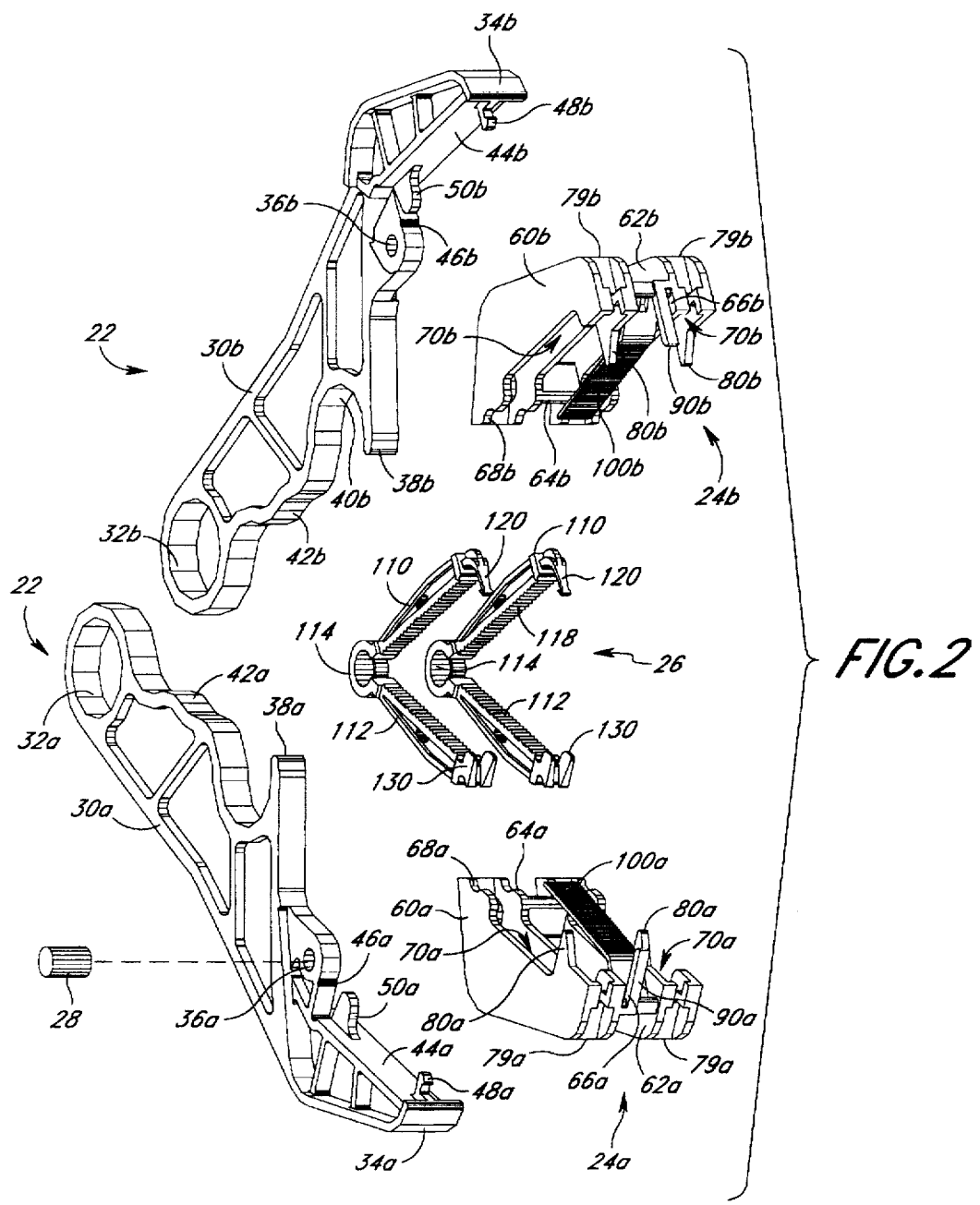
FIG. 2 is an exploded perspective view of a handle assembly, clamp holder assembly and clamps of FIG. 1.

As shown more clearly in the exploded view of FIG. 2, a rivet 28 is preferably used to attach a pair of substantially identical handle portions 30a,b comprising the handle assembly 22. In the drawings herein, the suffix "a" is used to denote the handle portion 30 extending toward the upper left of the drawing and elements of the device 20 attached to the upper portion 30a, and the suffix "b" is used to denote the handle portion 30 extending toward the lower left of the drawing and the elements attached thereto. The description and drawing reference numerals herein not bearing either suffix indicates applicability to elements of either/both portions of FIG. 2.

Figure 3:
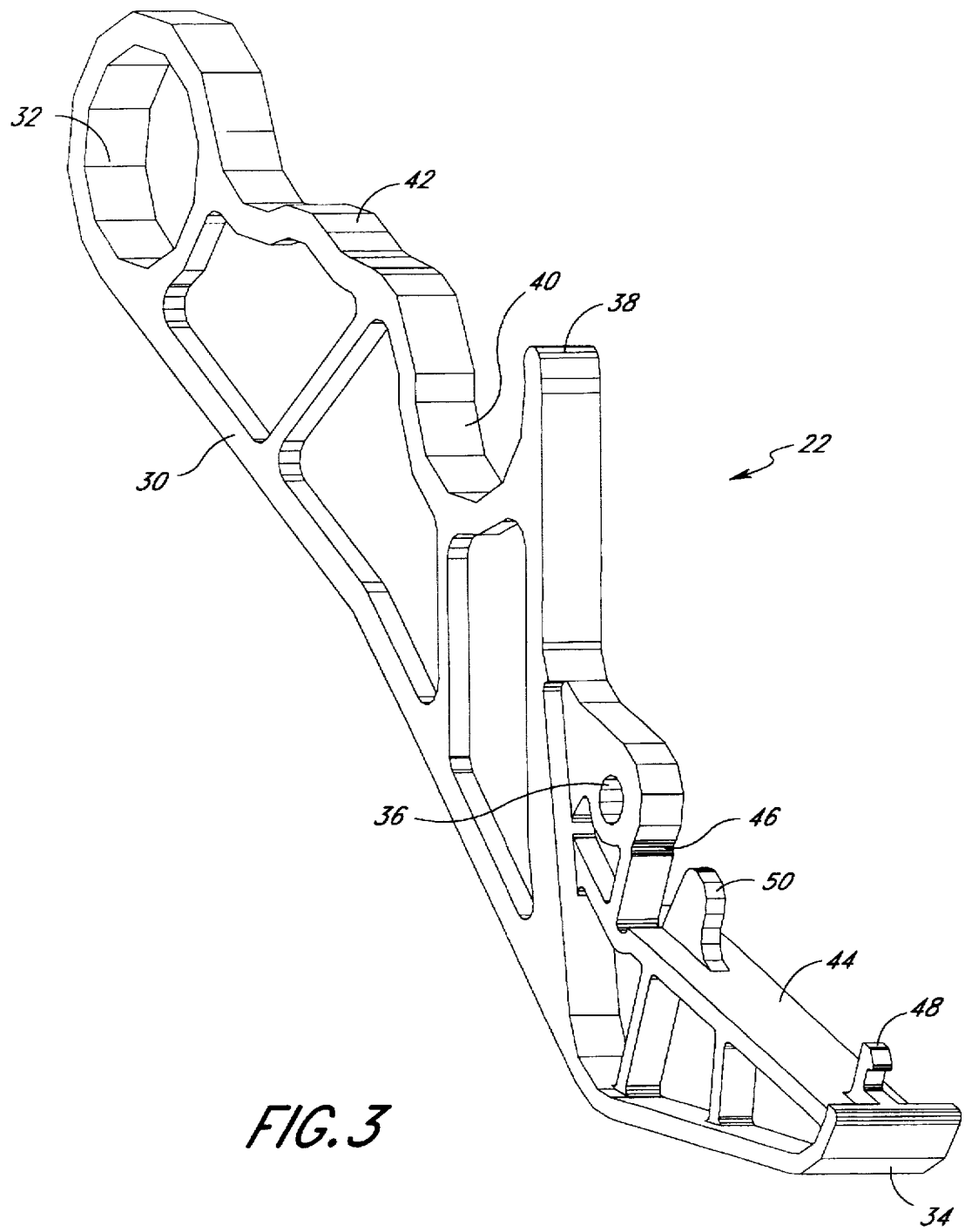
FIG. 3 is a perspective view of one handle portion of the handle assembly.

Referring to FIG. 3, each handle portion 30 comprises a hole 32 at the proximal end for receiving a littlest finger or pinky of the user. An extension 34 bounding the holder assembly 24 is at the distal end of the portion 30, and a hole 36 for receiving the rivet 28 is at a position intermediate the pinky hole 32 and the extension 34. A protuberance 38 proximal to the hole 36 provides a place for pressure by the user's thumb for release of the device 20 from the clamped cord, described later. A thumb rest area 40 of the portion 30 is just proximal the protuberance 38. The user's palm or remaining three fingers press against a curved portion 42 between the pinky hole 32 and the thumb rest area 40. A detailed description of the positioning of the user's hand on the handle portions 30a,b is later described herein.

Clamp Holder Assembly

Figure 4:
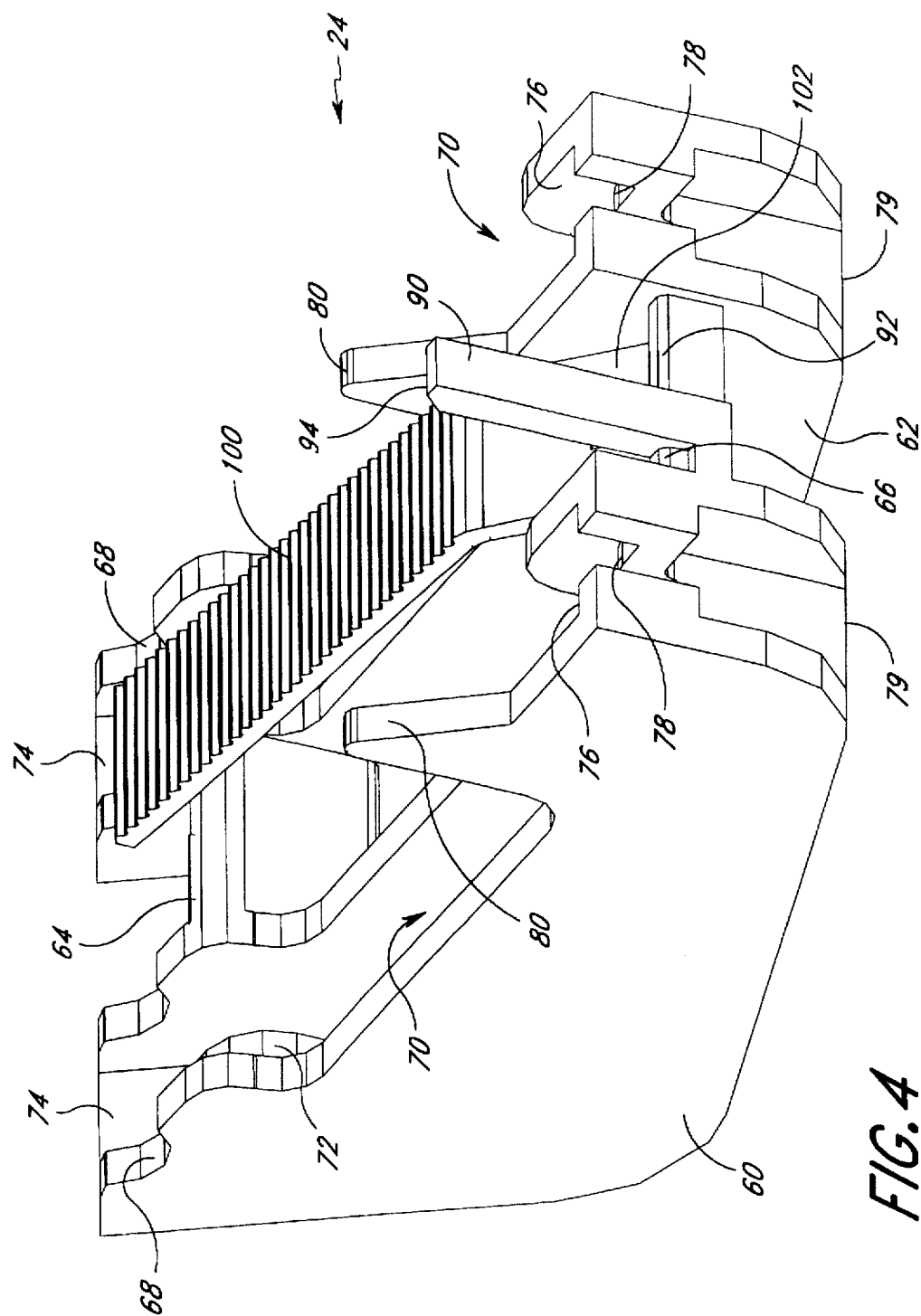
FIG. 4 is a perspective view of one holding member of the clamp holder assembly.

In the preferred embodiment, the holder assembly 24 comprises a pair of substantially identical holding members or holders 60 which are each snapped onto a support 44 of the handle portion 30 (FIG. 3). As shown in FIG. 4, each holder includes a longitudinal opening or space 62 for receiving the support 44 and is positioned and held by an indentation 46 and a hook 48 at the proximal and distal ends, respectively, of the support 44 of the handle portion 30, shown in FIG. 3. A ledge 64 at the proximal end of the holder 60 sits in the indentation 46, and the hook 48 catches a ledge 66 at the distal end of the holder 60. Each holder has semicircular, concave portions 68 at its proximal end to provide clearance for the rivet 28. In an alternative embodiment, the holders 60 may be integrally formed with the handle portions 30, so that the device 20 comprises two substantially identical handle holder portions attached by the rivet 28 instead of the separate handle portions 30 and holders 60 described herein.

Referring again to FIG. 4, the clamps 26 shown in FIGS. 1 and 2 are received in receptacles 70 located to either side, laterally, of the space 62. Each receptacle 70 is bounded at a proximal end by a proximal wall 74 of the holder 60 having a convex portion 72 and at a distal end by a lateral slot 76 and a step 78. The portion 72 abuts the hinged portion of the clamp 26, and the slot 76 allows entry of either of the free ends of the clamp such that the step 78 subsequently retains that end within the receptacle 70. As discussed below, the pre-existing bias of the clamps provides the necessary pressure to maintain the clamps 26 in the receptacles 70. The receptacle 70 has a depth allowing each arm of the clamp 26 to flex or bow outwardly with respect to the inner surface of each arm, without restriction by a floor 79 of the receptacle 70, when even a thick cord 10 is clamped.

In order to facilitate the proper placement of the cord 10 within the mouth formed by the holder assembly 24 of the device 20, without the need to view this placement, a pair of inverted V-shaped guides 80 are laterally positioned on each holder 60. These guides 80 help prevent the cord 10 from being pushed out from the apex of the mouth formed by the holder assembly 24 as it is closed such that the cord 10 does not interfere with the complete closure of the clamps 26.

An indicator 90, preferably comprising a columnar member at a distal end of each holder 60, provides assurance that the clamps 26 have been adequately secured onto the cord 10. The indicator 90 is positioned somewhat off center, adjacent an interference step 92 which contacts the opposing holder's indicator 90. As the holders 60 are brought together by the user's manipulation of the handle portions 30, a beveled portion 94 of each indicator 90 contacts and then passes distally outside of the step 92. The increased pressure felt by the user as the indicator 90 contacts the step 92 is a first indication of closure, and a snapping sound of the portion 94 as it is pressed past the step 92 is a second indication. The third indication of complete closure is the visible bend of the indicators 90 over the steps 92.

Pressure Plates

Figure 6:
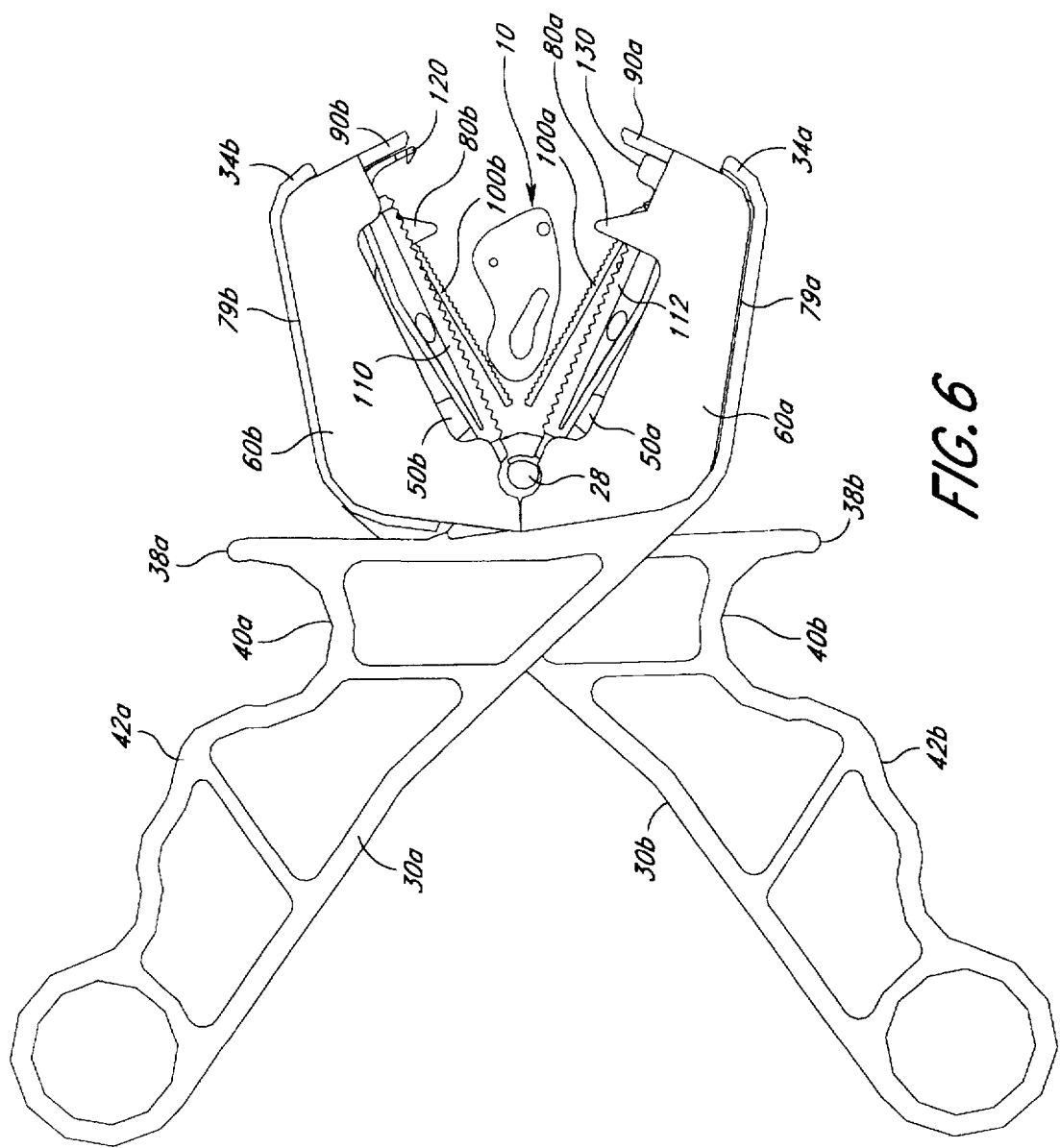
FIG. 6 is a side elevational view of the device showing a preferred embodiment wherein opposing pressure plates in the holder assembly make first contact with the cord.

Shown in FIG. 4, and illustrated in use in FIG. 6, is a pressure plate 100 which is cantilevered substantially over the space 62 of each holder 60, between the receptacles 70. The plate 100 is generally rectangular and is attached by a strip 102 to the holder 60 at its distal end, just proximal to the indicator 90 and step 92. Preferably, the plate 100 has ridges or grooves on a substantial portion of its exterior surface. Most preferably, the free or proximal end of the plate 100 is positioned above the level of the ledge 64 of the holder 60, and is about ¼ inch above a rib 50 protruding from the support 44 of the handle portion 30. The rib 50 extends into the proximal end of the space 62 and restricts the motion of the proximal end of the plate 100, contacting it so that it forms a dually-constrained beam when the device 20 is closed over the cord 10.

Umbilical Cord Clamps

Figure 5B:
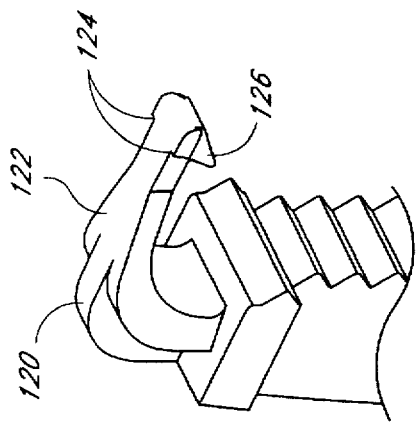
FIGS. 5b and 5c are detail perspective views of latch and lock ends, respectively.
Figure 5C:
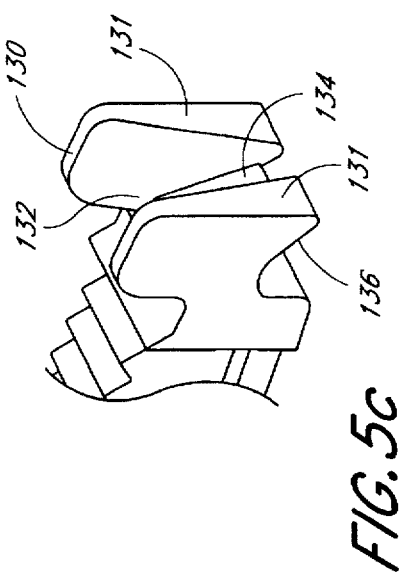
Figure 5A:
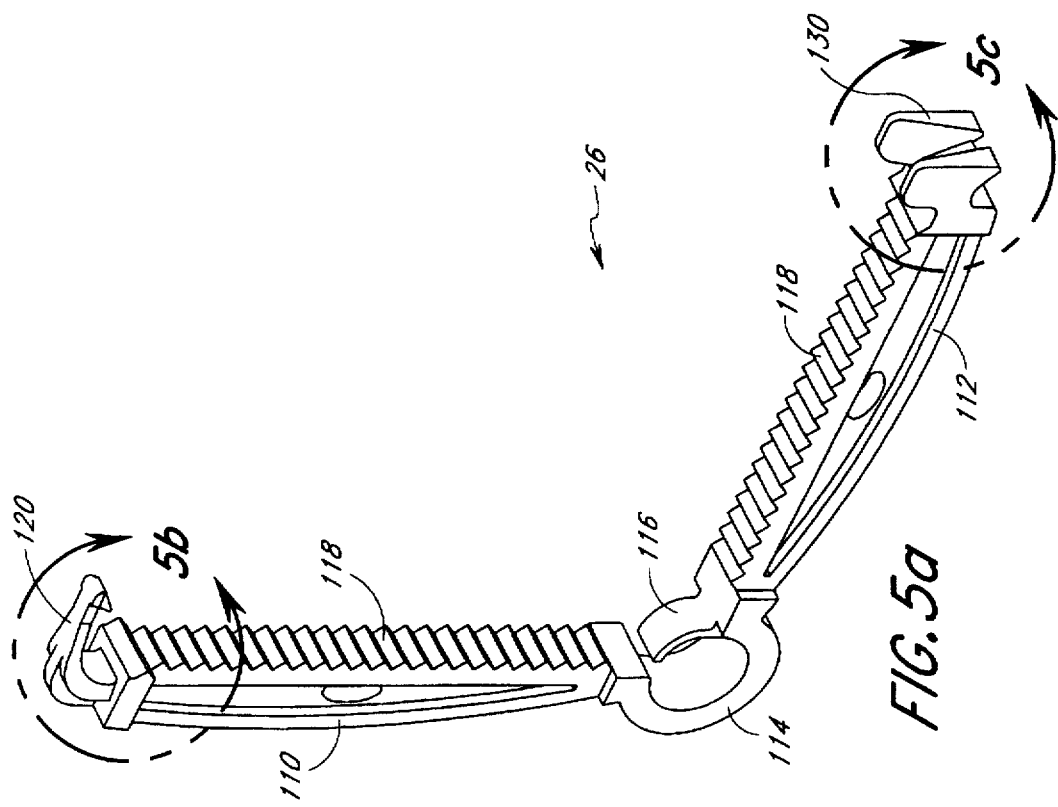
FIG. 5a is a perspective view of one exemplary clamp for use with the device of the present invention.

Referring now to FIGS. 5a–5c, details of the configuration of a preferred clamp 26 are shown. However, it is understood that other commercially available clamps well known to those skilled in the art may be used in alternative embodiments of the present invention. The clamp 26 preferably comprises a pair of arms 110, 112 joined at a hinge portion 114 having a closure tab 116. Interior surfaces of the arms 110, 112 have ridges 118 for securely gripping the cord 10. One arm 110 has a latch 120 and the other arm 112 has a lock 130.

The clamp 26 is manufactured such that the arms 110, 112 are substantially orthogonal to one another, thus providing the means by which the clamp is retained within the holders 60 in assembly, since the holders 60 of the device 20 open only up to a 50 degree separation. In the device 20 of the present invention, the pair of clamps 26 contained within the holder assembly 24 are not necessarily positioned to have the same arms 110 or 112 within the same holder 60, as is shown herein, and may have the positions of the clamps 26 reversed without loss of the advantages of the present invention.

Referring to the detail view of FIG. 5b, the latch 120 is comprised of an extension 122 formed approximately orthogonal to the arm 110. At the end of the extension 122 are laterally extending tabs 124 and an inwardly extending tab 126. The latch 120 is somewhat hook-like and is received into the lock 130 between side walls 131. The tab 126 of the latch 120 fits through a channel 132 formed by the walls 131 and a sloped portion 134. The tabs 124 follow over the walls 131 and sloped portion 134. The extension 122 is slightly longer than the portion 134 to ensure that the tab 126 can extend past and be caught by notched wall ends 136 at the end of the portion 134.

Operation

FIG. 6 illustrates the operation of the preferred embodiment of the present invention, in which the pressure plates 100 make first contact with the cord 10 to begin squeezing the blood outwardly from between the two clamps 26 after which the clamps 26 are secured to the cord 10. In an alternative embodiment (not shown), the pressure plates can make contact with the cord 10 substantially simultaneously with the clamps 26 without departing from the spirit of the present invention. It can be seen in FIG. 6 that the holders 60 of the device 20 are placed substantially perpendicular around the cord 10 with a maximum opening of the holders 60 of about 50 degrees. The device 20 is positioned so that the cord 10 is generally between the rivet 28 at the apex of the device opening and the guides 80 of the holder assembly 24. Although the device 20 is shown with the latch 120 of the clamp 26 at the top and the lock 130 at the bottom, the positioning of the arms 110, 112 does not affect the operation or advantages of the present invention.

With the user's thumb received in the area 40a, and his or her pinky in the hole 32b, the proximal halves of the handle portions 30a,b are pressed together such that the holder 60b of the assembly 24 is brought downward and the holder 60a is brought upward thereby pushing the plates 100a,b onto the cord 10. The proximal end of each plate 100a,b is bent into the holder 60a,b by resistance from the cord 10. The plate end is restrained from further motion by the rib 50a,b.

Figure 7:
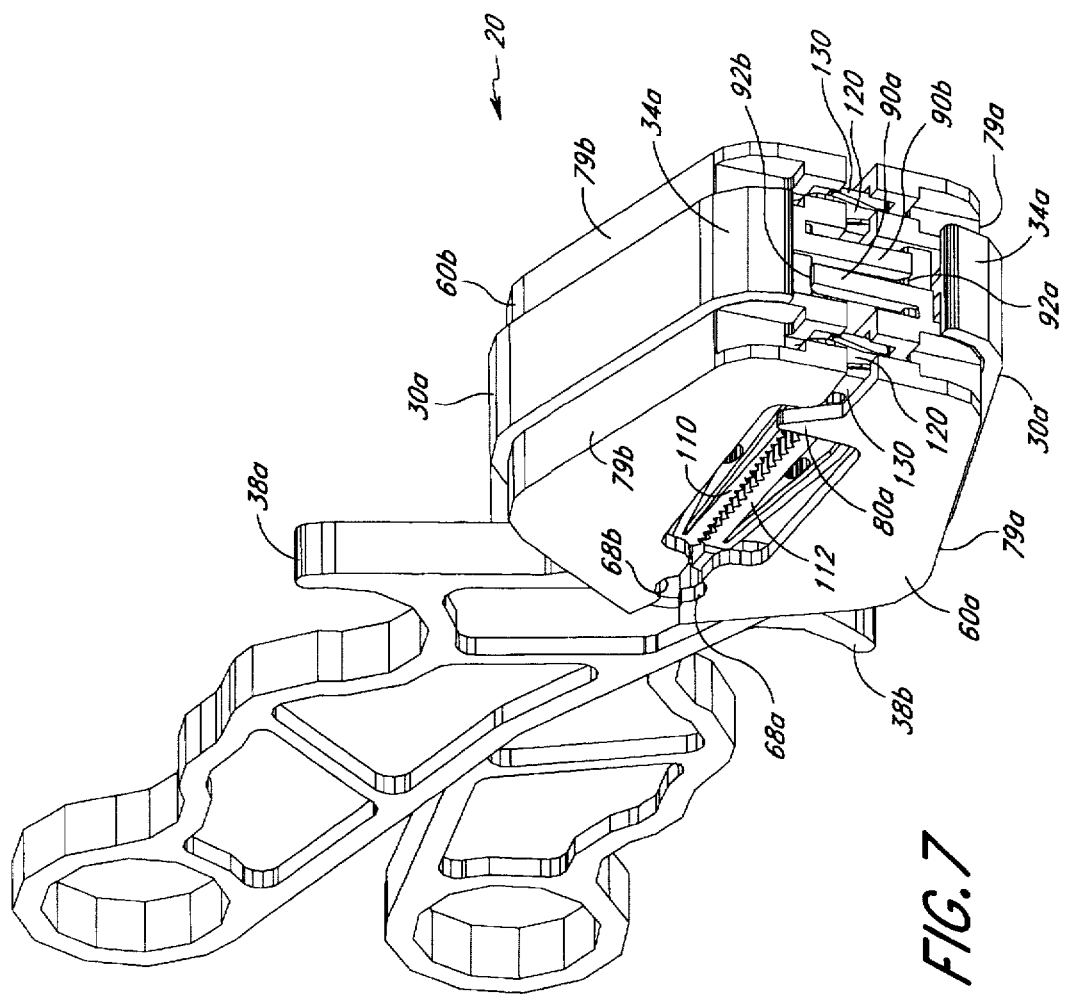
FIG. 7 is a perspective view of the device in a closed position.

As the holders 60a,b are closed further together, the plates 100a,b each act as dually-constrained beams and compress the cord 10 therebetween, squeezing blood out from between the plates 100a,b. At about 10 degrees of closure of the holders 60a,b, the ridges 118 of the clamp arms 110, 112 contact and begin to securely grip the cord 10 at each side, laterally, of the plates 100a,b. The user may then use his or her palm, rather than thumb, to provide additional pressure for closure of the device 20. At about 5 degrees of closure, the latches 120 make contact with the locks 130 of the clamps 26, and the holder indicators 90a,b make contact with the steps 92b,a, respectively. FIG. 7 shows complete closure of the clamps 26 and holder assembly 24 without a cord 10 therein. Once the clamps 26 are fully engaged on the cord 10, there is little or no worry of blood squirting from the compressed section between the clamps 26.

To release the holder assembly 24 from the clamps 26 and cord 10, the user exerts force on the protuberance 38a using his or her thumb so that the indicators 90a,b come off the steps 92b,a, respectively, and the holders 60a,b separate from each other. The bias of the plates 100a,b provides additional force to separate the holders 60a,b. Since the latches 120 and locks 130 are engaged, the clamps 26 remain secured on the cord 10 and slip easily out of the receptacles 70a,b. The holder assembly 24 is then fully opened to about 50 degrees and removed from the area of the cord 10. The low cost of the device 20 makes it possible to dispose of it after use, rather than having to sterilize and store it for reuse as an economy measure.

After the clamps 26 have been secured to the umbilical cord 10, and the clamping device 20 has been removed, the doctor or nurse may then verify for his or her self that the umbilical cord 10 is ready to be severed between the pair of clamps 26. A conventional cutting device is then used to cut the cord 10 without the worry of any significant amount of blood being released, since most of the blood has already been squeezed away from between the pair of clamps 26 by the pressure plates 100 of the device 20. In this manner, a new, separate being (infant) is brought into the world.

Previous umbilical cord clamping devices serve to further pressurize and squirt the blood out from between the clamps, especially when the device cannot contain the volume of blood that is released. These devices are also often compatible only with specially designed clamps, or are of a complex design resulting in a higher cost. In contrast, the umbilical cord clamping device of the present invention removes blood from between a pair of clamps so that little or no blood issues upon the cutting of the cord.

In summary, the present device is generally similar in operation to other obstetrical tools (i.e., pliers-like) and affords easy, single-handed operation. The present device may have molded integral holders and handle portions, or the holders and handle portions may be separately formed and attached together in an easy assembly process. The ergonomic handle design allows leverage by the palm of the user so that even a smaller or less strong hand can easily provide the force to attach the clamps to the umbilical cord. The device of the present invention can be manufactured at a cost low enough to allow disposability of the device after use, so that sterilization is not a concern.

The pressure plates compress the cord to remove blood from between the clamps and minimize blood splatter. Preferably, the plates make first contact with the cord, prior to the clamps. In the preferred embodiment, the limit of an approximately 50 degree opening of the holder assembly provides retention of resilient clamps which are originally molded to about a 90 degree configuration. The provision of closure indicators includes tactile, aural and visual assurance that the clamps are adequately secured to the cord. The provision of cord guides in the present invention allows non-angled clamping, so that precise positioning of the device around the cord is not necessary to ensure proper placement of the clamps, and so the cord does not interfere with the clamp closure. The procedure of clamping before cutting allows a doctor or nurse to view the cord prior to its severance, and perhaps prior to allowing the father to cut the cord.

The embodiments illustrated and described above are provided merely as examples of the umbilical cord clamping device of the present invention. Other changes and modifications can be made from the embodiments presented herein by those skilled in the art without departure from the spirit and scope of the invention, as defined by the appended claims.

What is claimed is:

1. A clamping device for single-handed attachment by a user of a pair of resilient clamps onto an umbilical cord of a newly born infant prior to severance of said cord, said clamping device squeezing blood away from between said resilient clamps so that said cord can be severed with release of a minimal amount of blood, said clamping device comprising:

a handle assembly comprising a pair of substantially identical handle portions having proximal ends for grasping by said user; and a clamp holder assembly comprising a pair of substantially identical holding members each comprising a pair of receptacles and a pressure plate positioned between said receptacles, one of said holding members attached to a distal end of one of said handle portions and the other of said holding members attached to a distal end of the other of said handle portions, said plate positioned exterior to said receptacles and said resilient clamps such that said plates make first contact with said cord during operation of said device, each of said resilient clamps comprising a pair of arms being received into said receptacles of said holding members;

said resilient clamps being retained within said holder assembly prior to closure of said resilient clamps by compression of said arms by said holding members, said pressure plates being juxtaposed to compress said cord to squeeze blood away from between said resilient clamps thereby substantially eliminating said blood from said cord between said resilient clamps so that severance of said cord can be performed with release of a minimal amount of blood, said resilient clamps being readily released from said members after said closure.

2. A clamping device for single-handed attachment by a user of a pair of resilient clamps onto an umbilical cord of a newly born infant prior to severance of said cord, said clamping device squeezing blood away from between said resilient clamps so that said cord can be severed with release of a minimal amount of blood, said clamping device comprising:

a handle assembly comprising a pair of substantially identical handle portions comprising proximal ends for grasping by said user; and a clamp holder assembly comprising a pair of substantially identical holding members each comprising a pair of receptacles and a pressure plate positioned between said receptacles, one of said holding members attached to a distal end of one of said handle portions and the other of said holding members attached to a distal end of the other of said handle portions, each of said resilient clamps comprising a pair of arms being received into said receptacles of each of said members;

said resilient clamps being retained within said holder assembly prior to closure of said resilient clamps by compression of said arms by said holding members, said pressure plates being juxtaposed to compress said cord to squeeze blood away from between said resilient clamps thereby substantially eliminating said blood from said cord between said resilient clamps so that severance of said cord can be performed with release of a minimal amount of blood, said resilient clamps being readily released from said members after said closure.

3. A clamping device for single-handed attachment by a user of a pair of resilient clamps onto an umbilical cord of a newly born infant prior to severance of said cord, said clamping device squeezing blood away from between said resilient clamps so that said cord can be severed with release of a minimal amount of blood, said clamping device comprising:

a handle assembly comprising a pair of substantially identical handle portions comprising proximal ends for grasping by said user; and a clamp holder assembly comprising a pair of substantially identical holding members each comprising a pair of receptacles, a pressure plate positioned between said receptacles and a closure indicator, one of said holding members attached to a distal end of one of said handle portions and the other of said holding members attached to a distal end of the other of said handle portions, each of said resilient clamps comprising a pair of arms being received into said receptacles of each of said members;

said resilient clamps being retained within said holder assembly prior to closure of said resilient clamps by compression of said arms by said holding members, said pressure plates being juxtaposed to compress said cord to squeeze blood away from between said resilient clamps thereby substantially eliminating said blood from said cord between said resilient clamps so that severance of said cord can be performed with release of a minimal amount of blood, said indicators providing tactile, aural and visual feedback of sufficient closure of said pair of resilient clamps to prevent flow of blood therebetween, said resilient clamps being readily released from said members after said closure.

4. A clamping device for single-handed attachment by a user of a pair of resilient clamps onto an umbilical cord of a newly born infant prior to severance of said cord, said clamping device squeezing blood away from between said resilient clamps so that said cord can be severed with release of a minimal amount of blood, said clamping device comprising:

a handle assembly comprising a pair of handle portions comprising proximal ends for grasping by said user; and a clamp holder assembly comprising a pair of holding members each comprising a pair of receptacles and a pressure plate positioned between said receptacles, one of said holding members attached to a distal end of one of said handle portions and the other of said holding members attached to a distal end of the other of said handle portions, each of said resilient clamps comprising a pair of arms being received into said receptacles of each of said members;

said pressure plates being juxtaposed to compress said cord to squeeze blood away from between said resilient clamps thereby substantially eliminating said blood from said cord between said resilient clamps so that severance of said cord can be performed with release of a minimal amount of blood.

5. The clamping device of claim 4, wherein said plates are positioned exterior to said receptacles and said resilient clamps such that said plates make first contact with said cord during operation of said device.

6. The clamping device of claim 4, wherein said plates are attached at a first end to said holding members and are initially unconstrained at a second end thereby being cantilevered prior to operation of said device.

7. The clamping device of claim 4, wherein said pair of arms of each of said resilient clamps are initially formed at about a 90 degree angle to each other and said holding members of said device are limited to opening to approximately 50 degrees therebetween thereby compressing and retaining said arms of said resilient clamps therein.

8. The clamping device of claim 4, wherein said members of said holder assembly further comprise a closure indicator providing tactile, aural and visual feedback of sufficient closure of said resilient clamps onto said umbilical cord to prevent flow of said blood therebetween.

9. The clamping device of claim 4, wherein said members of said holder assembly include guides for positioning said cord within said device during said closure of said resilient clamps.

10. The clamping device of claim 4, wherein said members of said holder assembly are snapped onto said distal ends of said handle portions and a rivet is used to attach said handle portions together at a pivot point for rotation of said handle assembly thereabout.

11. The clamping device of claim 4, wherein said handle portions of said handle assembly and said members of said holder assembly are integrally formed whereby said device comprises a pair of one-piece handle holder sections attached together at a pivot point.

12. The clamping device of claim 4, wherein a pivot point is located in a section intermediate said proximal and distal ends of said handle portions, each of said handle portions comprising a hole formed on said proximal end and a protuberance located between said proximal end and said pivot point, said hole on one of said handle portions receiving a finger of a hand of said user, a thumb of said hand pressing against said protuberance on the other of said handle portions for removal of said members from said resilient clamps after said closure.

13. A clamping device for single-handed attachment by a user of a pair of clamps onto an umbilical cord of a newly born infant prior to severance of said cord, said clamping device comprising:

a pair of resilient clamps each comprising a pair of arms; and a handle holder assembly, comprising:

a pair of substantially identical handle portions comprising proximal ends for grasping by said user, said handle portions attached together at a pivot point; and a pair of substantially identical holders each comprising a pair of receptacles for receiving one arm of each of said pair of clamps and a pressure plate positioned between said pair of receptacles, each of said holders attached to a distal end of each of said handle portions;

wherein said resilient clamps are retained within said holders prior to closure of said resilient clamps by compression of said arms and said plates are juxtaposed to compress said cord to squeeze blood away from between said resilient clamps thereby substantially eliminating said blood from said cord between said resilient clamps, said severance performed with release of a minimal amount of blood, said resilient clamps readily released from said holders after said closure.

14. The clamping device of claim 13, wherein said plates are positioned exterior to said receptacles and said resilient clamps such that said plates make first contact with said cord during operation of said device.

15. The clamping device of claim 13, wherein said plates are attached at a first end to said holders and are initially unconstrained at a second end thereby being cantilevered prior to operation of said device.

16. The clamping device of claim 13, wherein said holders form a closure indicator providing an aural and visual feedback of sufficient closure of said resilient clamps onto said cord to prevent flow of said blood therebetween.

17. The clamping device of claim 13, wherein each of said pair of arms are originally formed orthogonal to each other and said holders of said device are limited to opening to approximately 50 degrees, thereby compressing and retaining said arms of said resilient clamps therein.

18. The clamping device of claim 13, wherein said holders are snapped onto said distal ends of said handle portions and a rivet is used to attach said handle portions together at said pivot point for rotation of said assembly thereabout.

19. The clamping device of claim 13, wherein said handle portions and said holders are integrally formed whereby said device comprises a pair of one-piece sections attached together at said pivot point and receiving said resilient clamps.

20. The clamping device of claim 13, wherein said holders include guides for positioning said cord within said device during said closure of said resilient clamps.

21. A clamping device for single-handed attachment by a user of a pair of clamps onto an umbilical cord of a newly born infant prior to severance of said cord, said clamping device substantially reducing the amount of blood in said cord between said pair of clamps so that the amount of blood squirting out upon said severance is minimized, said clamping device comprising:

a pair of resilient clamps; and a handle holder assembly, comprising:
means for said user to operate said clamping device;
means for supporting said pair of clamps on said assembly; and
means for providing pressure on said umbilical cord between said pair of clamps thereby squeezing said cord between said pair of clamps and substantially eliminating said blood from said cord between said resilient clamps;

said severance of said umbilical cord performed with release of a minimal amount of blood.

22. A clamping device for single-handed attachment by a user of a pair of clamps onto an umbilical cord of a newly born infant prior to severance of said cord, said clamping device substantially reducing the amount of blood in said cord between said pair of clamps so that the amount of blood squirting out upon said severance is minimized, said clamping device comprising:

a pair of resilient clamps; and a handle holder assembly, comprising:
handle portions for said user to operate said clamping device;
holders for supporting said pair of clamps on said assembly; and
pressure plates for compressing said umbilical cord between said pair of clamps thereby squeezing and substantially eliminating said blood from said umbilical cord between said pair of clamps;

said severance of said umbilical cord performed with release of a minimal amount of blood.

23. A method of clamping and cutting an umbilical cord of a newly born infant with release of a minimal amount of blood from said cord upon said cutting, said method comprising the steps of:

a) inserting a pair of resilient clamps into receptacles of a clamping device, said clamping device comprising holders having juxtaposed pressure plates positioned between said receptacles;

b) positioning said clamping device about said umbilical cord such that said pair of clamps define a cutting section therebetween;

c) closing said clamping device so that said pressure plates compress said cutting section to remove most of said blood from between said pair of clamps, said pair of clamps closing sufficiently to be secured to said cord thereby preventing slippage of said resilient clamps off said umbilical cord;

d) removing said clamping device from said umbilical cord, said pair of clamps remaining on said cord; and e) severing said umbilical cord at said cutting section between said pair of clamps with minimal blood issuing therefrom.

24. The method of claim 23, wherein Step c) comprises closing said clamping device so that said pressure plates make contact with and squeeze said cord prior to closure of said resilient clamps.

25. The method of claim 23, wherein Step c) comprises closing said clamping device by applying pressure thereon until indicators on said holders are felt, heard and seen to indicate sufficient closure.

26. The method of claim 23, wherein Step b) comprises placing said holders around said cord using guides on said holders to ensure said cord remains sufficiently within said clamping device.

27. The method of claim 23, wherein each of said pair of clamps comprises a pair of arms substantially at right angles to one another, said holders of said clamping device limited to opening to about 50 degrees, Step a) comprising inserting said arms of said pair of clamps into said holders such that said resilient clamps are retained in said holders by said arms pressing against said holders.

28. A method of clamping and cutting an umbilical cord of a newly born infant with release of a minimal amount of blood from said cord upon said cutting, said method comprising the steps of:

a) inserting a pair of resilient clamps into receptacles of a clamping device, said clamping device comprising holders having juxtaposed pressure plates positioned between said receptacles;

b) securing said pair of clamps onto said umbilical cord by closing said clamping device such that said pressure plates squeeze said umbilical cord between said pair of clamps thereby substantially eliminating blood therefrom; and c) severing said umbilical cord between said pair of clamps with minimal blood issuing therefrom.

* * * * *